United States Patent [19]

Williams

[11] Plant 4,360

[45] Jan. 2, 1979

[54] ROSE PLANT

[76] Inventor: J. Benjamin Williams, 2800 Elnora St., Silver Spring, Md. 20902

[21] Appl. No.: 875,587

[22] Filed: Feb. 6, 1978

[51] Int. Cl.[2] ..... A01H 5/00

[52] U.S. Cl. ..... Plt./7

[58] Field of Search ..... Plt./7

*Primary Examiner*—Robert E. Bagwill

[57] ABSTRACT

A novel rose of the mini-flora (R) class characterized by its compact growth and blooms which are a blend of yellow, peach, pink and ivory, with a brilliant orange-red reverse.

1 Drawing Figure

The present invention relates to a new and distinct variety of rose plant of the mini-flora (R) rose class, which was originated by my crossing as seed parent a rose seedling derived from a cross between the rose variety known as "Circus" (U.S. Plant Pat. No. 1,382) and the rose variety known as "Sweet Repose" (nonpatented) and a rose seedling derived from a cross between the rose variety known as "Little Darling" (U.S. Plant Pat. No. 1,581) and the rose variety known as "Starina" (U.S. Plant Pat. No. 2,646).

Among the novel characteristics possessed by this new variety which distinguish it from its parents and all other varieties of which I am aware are: (1) its low and compact habit of growth. It is best described as being a larger and stronger grower than the miniature rose and a smaller and more compact grower than the fluoribunda rose producing a small perfectly formed flower bud that opens to no more than one inch when fully open, (2) the cheerful blending of yellow, pink peach, and orange-red coloring of the inner petal surfaces, (3) flowers are produced on a short blooming cycle holding their color well on the plant and after cutting, having petals that drop off cleanly on aging, and (4) a small compact vigorous plant which is "winter hardy" and produces flowers borne singly and several together as sprays. Asexual reproduction by budding of the new variety as performed in Chester County, Pa., shows that the foregoing and other distinguishing characteristics come true to form and are established and transmitted through succeeding propagations.

The new and improved rose variety which I have developed is an unusually vigorous low compact growing mini-flora (R) rose with unusual cheerful blending of colors that keep their substance. The flowers have excellent bud form and open well in varied weather conditions. The color of the blooms holds well and the appearance is not adversely affected by rain or heat. A sweet fresh tea fragrance compliments the beauty of the flowers.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "45B" is plate 45B of the Royal Horticultural Society Color Chart.

Parentage: Seedling.

*Seed parent.*—An unnamed seedling resulting from a cross between "Circus" × "Sweet Repose".

*Pollen parent.*—An unnamed seedling resulting from a cross between "Little Darling" × "Starina".

Class: Mini-flora (R) (dwarf floribunda).

The following observations are made of specimens grown in Chester County, Pa., during the month of June.

1. FLOWER

Blooming habit: Continuous.

A. Bud:

(1) *Size.*—Small.

(2) *Form.*—Pointed.

(3) *Color.*—When sepals first divide — 8C with a heavy washing of 44B. When petals begin to unfurl — 8D. When half-blown: inside of petals — 19D with marking of 44B on edge of petals; reverse side of petals — 19D with 44B washing.

(4) *Sepals.*—Medium, tapered, curling back as bud opens extending beyond the length of the unopen bud. Sepals color: inside — 148D; outside — near 143D.

(5) *Peduncle.*—Length — 1 to 1½ inches. Strength — erect, much short branching with side buds from below peduncle. Color — near 146C with heavy overcast of 178A. Aspect — Smooth.

B. Bloom:

(1) *Size.*—Average size when fully expanded — not more than 1 inch.

(2) *Borne.*—Singly and several together in sprays of 3 to 7 blooms.

(3) *Form.*—Pointed, high centered; petals slightly notched rolling outward becoming ruffled at maturity; excellent bud form and to ¾ open, flower holds well.

(4) *Petalage.*—Number of petals under normal conditions — 18.

(5) *Color (during first two days).* —Inner petals at center of flower — 19C. Outer petals — near 19D with 44B marking. Base of petals (point of attachment) — 8B. Reverse of petals — 8C with 44C washing. General tonality from a distance — near a blending of ivory peach with pink to orange red overcast.

(6) *Color change: as bloom ages.*—Center of inner petal takes on a white to peach ivory cast of 19C with 44D marking. Color holds well cut or on bush. General tonality three or more days — 19D with upper surface and edge of petals washed with 44D.

C. Petals:

(1) *Texture.*—Thick.

(2) *Appearance.*—Inside — velvety. Outside — satiny with lots of substance, not effected by rain or heat.

(3) *Form.*—Rounded slight notching.

(4) *Arrangement.*—Imbricated, regularly arranged.

(5) *Petaloids in center.*—Very few, small.

(6) *Persistence.*—Drop off cleanly.

(7) *Fragrance.*—Sweet fresh tea.

(8) *Lasting quality.*—Very good on plant and as cut flower and hold their cheerful color.

2. REPRODUCTIVE ORGANS

A. Stamens, filaments and anthers:

(1) *Arrangement.* —Medium size, regularly arranged around styles.

(2) *Color.* —22C.

B. Pollen: Color — 22B.

C. Styles: Bunched, uneven, short, thin.

D. Stigmas: Color — pink cast orange red 34B.

E. Hips:

*Shape.*—Globular.

*Size.*—Small.

*Color.* —169C.

*Do seeds protrude.*—Slight.

3. PLANT

A. Form: Spreading compact.

B. Growth: Very vigorous, uniform low branching plant, new growth occurs regularly through season. Height attained — 12 to 18 inches at maturity.

C. Foliage: Compounded 3 to 5 leaflets on single blooms and sprays of 5 to 7 leaflets on main canes (plant and foliage growth similar to that of the floribunda rose except much more dwarfed and close to the ground).

(1) *Size.*—Small.

(2) *Quantity.*—Abundant, cover plant to ground.

(3) *Color.*—New foliage: Upper side — near to 178B with deep bronze green veining. Under side — greenish red with 183C overcast. Old foliage: Upper side — holly green somewhat near 137A. Under side — 137C.

(4) *Shape.*—Oval, pointed.

(5) *Texture.*—Upper side — leathery, glossy. Under side — smooth.

(6) *Edge.*—Serrated near tip.

(7) *Serration.*—Very small and uniform.

(8) *Leaf stem.*—Color — 137B. Under side — 137C.

(9) *Stipules.*—Medium smooth.

(10) *Resistance to disease.*—Blackspot — highly resistant. Mildew — highly resistant.

D. Wood:

(1) *New wood.*—Color — 137C. Bark — smooth.

(2) *Old wood.*—Color — 137B with a red bronze cast as it ages. Bark — smooth.

E. Thorns:

(1) *Thorns.*—Quantity — very few. On laterals from stalk — a few on main cane at base of plant. Form — flat base. Length — very small. Color (when young) — 148C. Position — irregular.

(2) *Prickles.*—Quantity — none.

F. Winter hardiness: Good winter hardiness, no protection needed.

I claim:

1. A new and distinct variety of rose plant of the mini-flora (R) class (dwarf-floribunda type) substantially as shown and described, characterized particularly by recurrent very small and well formed flowers borne singly and in sprays of 3 to 5 blooms having a cheerful blending of yellow, pink, peach and ivory with a brilliant orange-red cast on reverse of petals, on a well formed low compact plant, winter hardy and disease resistant, excellent for pot-forcing and use in tubs or planters for outside display.

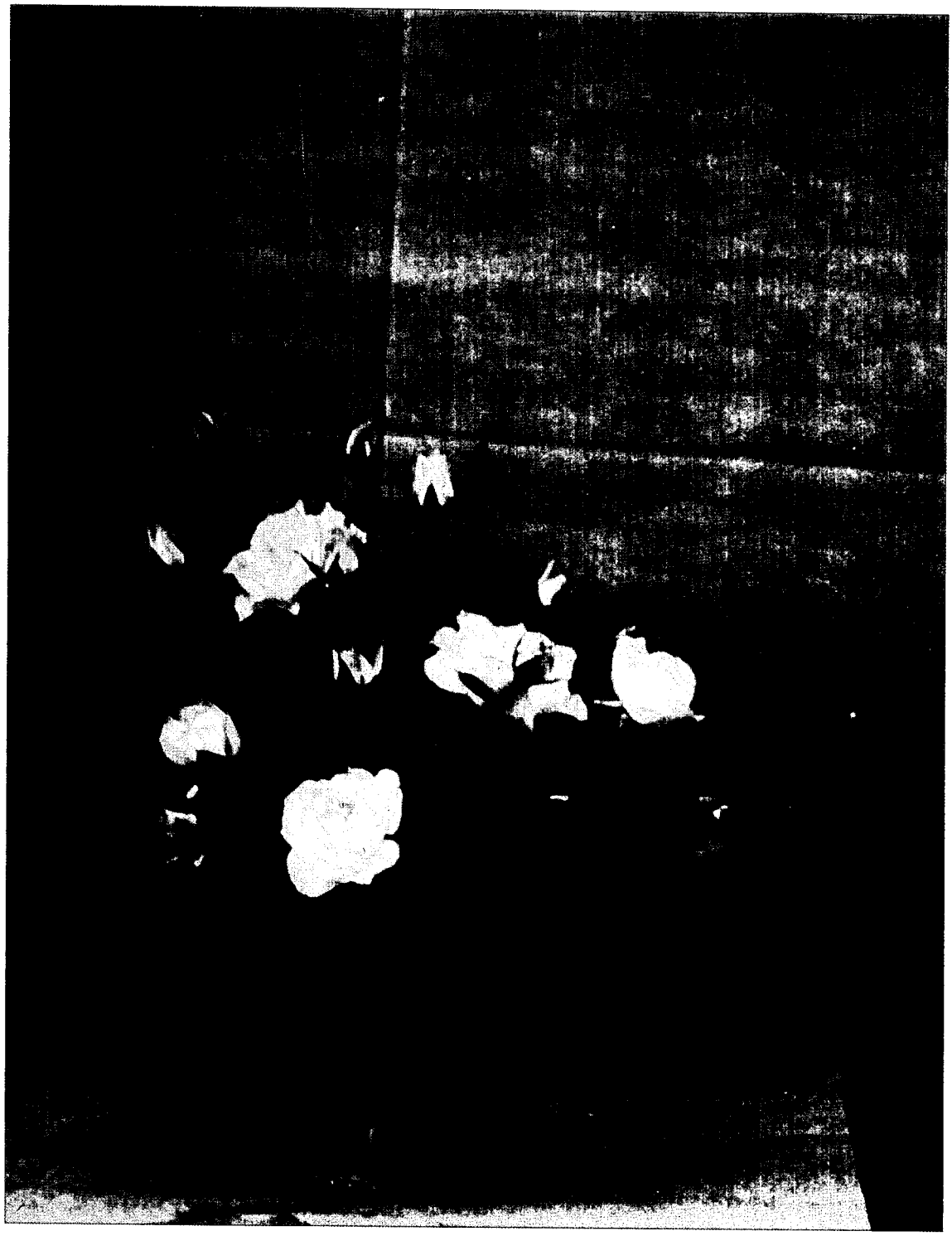

* * * * *